(12) United States Patent
Marsano et al.

(10) Patent No.: US 12,043,829 B2
(45) Date of Patent: Jul. 23, 2024

(54) UNGE PROMOTER SEQUENCE AND ITS USES

(71) Applicant: UNIVERSITA' DEGLI STUDI DI BARI ALDO MORO, Bari BA (IT)

(72) Inventors: René Massimiliano Marsano, Bitritto BA (IT); Antonio Palazzo, Mola di Bari BA (IT)

(73) Assignee: UNIVERSITA' DEGLI STUDI DI BARI ALDO MORO, Bari (IT)

( * ) Notice: Subject to any disclaimer, the term of this patent is extended or adjusted under 35 U.S.C. 154(b) by 0 days.

(21) Appl. No.: 18/145,042

(22) Filed: Dec. 22, 2022

(65) Prior Publication Data

US 2023/0203479 A1  Jun. 29, 2023

Related U.S. Application Data

(62) Division of application No. 16/715,451, filed on Dec. 16, 2019, now Pat. No. 11,788,084.

(51) Int. Cl.
| | |
|---|---|
| *C12N 15/11* | (2006.01) |
| *C12N 15/81* | (2006.01) |
| *C12N 15/85* | (2006.01) |

(52) U.S. Cl.
CPC ............... *C12N 15/11* (2013.01); *C12N 15/81* (2013.01); *C12N 15/85* (2013.01)

(58) Field of Classification Search
CPC ....................................................... C12N 15/11
See application file for complete search history.

(56) References Cited

U.S. PATENT DOCUMENTS 8,017,316 B2 *  9/2011  Tracey, Jr. ........ C07K 14/43581
                                                                 435/6.14

OTHER PUBLICATIONS

Cherbas et al., "Tools for Targeted Genome Engineering of Established *Drosophila* Cell Lines", Genetics, vol. 201, pp. 1307-1318. (Year: 2015).*

* cited by examiner

*Primary Examiner* — Suzanne M Noakes
(74) *Attorney, Agent, or Firm* — Silvia Salvadori

(57) ABSTRACT

The present invention relates to the field of biotechnologies and in particular to the use of a nucleotide sequence having transcription promoter activity in prokaryotic and eukaryotic cell systems.

2 Claims, 3 Drawing Sheets

Specification includes a Sequence Listing.

UNGE PROMOTER SEQUENCE AND ITS USES

RELATED APPLICATIONS

This application is a divisional application of U.S. Ser. No. 16/715,451 filed on Dec. 16, 2019, the content of which is incorporated herein by reference in its entirety.

STATE OF THE ART

The recombinant DNA technology allows the ectopic expression of nucleic acid sequences of interest, preferably gene sequences coding for a protein product, in host cell systems which normally do not express said gene sequences. This allows obtaining high levels of the protein of interest for the therapeutic, industrial or research use.

The ectopic expression, or else the forced expression of one or more nucleic acid sequences of interest in cell systems which normally do not express said nucleic acid sequences, is done by inserting at least one nucleic acid sequence of interest, for example at least one gene sequence, in an expression vector which then will be introduced in the selected host cell system.

The known host cell systems are both of prokaryotic origin, usually bacteria, and of eukaryotic origin, more complex both animal and plant cell systems, and the selection of the cell system depends on the type of protein which is intended to be expressed. The ectopic expression in the bacteria is the best option for producing high quantities of proteins at low production costs. However, eukaryotic systems need to be used when the protein requires post-translational modifications to keep its biological activity.

The expression vector is a nucleic acid molecule able to transport and drive the expression of DNA sequences of interest inside a host cell system.

It is imperative that the expression vector contains all the signals needed to the host cell system to transcribe the gene sequence of interest.

Among the signals the expression vector must contain, a key element is represented by the promoter.

The promoter is a nucleotide sequence which is upstream of the sequence coding for the gene of interest and is recognized by the RNA polymerase of the host cell system, which allows to start the transcription of sequences placed immediately downstream of it.

From the functional point of view, the promoter performs the same function both in the eukaryotic genomes and in the prokaryotic (bacterial) genomes but, from the structural point of view and the organization of the recognition sequences, the prokaryotic and eukaryotic promoters are definitely different.

At present the problem of the selection of the cell system requires that many different expression vectors must be used and "designed" ad hoc based on the cell system in which they will be used. To date, promoter sequences are not known which allow obtaining a high expression level of genes of interest both in prokaryotic cell systems and in eukaryotic cell systems. In fact, promoter sequences able to allow a high expression level of genes of interest in prokaryotic cell systems and in the yeast, which is an eukaryotic cell system, are not known.

EP2772539 describes two nucleic acid sequences of promoters able to express genes of interest in prokaryotic and eukaryotic cell systems.

However, said promoters show limitations both in terms of efficiency and in terms of functionality for the expression of the gene of interest in the yeast. Therefore, there's particular need of promoter sequences able to activate the expression of the gene downstream of them both in prokaryotic cells and in eukaryotic cells (including yeast). Furthermore, there is the need of expression vectors allowing high expression levels of genes in prokaryotic cell systems and in eukaryotic cell systems of different organisms.

OBJECTS OF THE INVENTION

It is a purpose of the present invention to provide a sequence having transcription promoter activity of a nucleic acid sequence of interest, for example a gene, in prokaryotic cell systems and eukaryotic cell systems.

It is also a purpose of the present invention to provide an expression vector which allows obtaining high expression levels of a nucleic acid sequence of interest in prokaryotic cell systems and eukaryotic cell systems.

It is another purpose of the invention to provide a method for expressing a sequence of interest in a prokaryotic and eukaryotic host cell system.

REFERENCE TO AN ELECTRONIC SEQUENCE LISTING

The contents of the electronic sequence listing (191083US2.xml; Size: 8,311 bytes; and Date of Creation: Dec. 22, 2022) is herein incorporated by reference in its entirety.

DESCRIPTION OF THE INVENTION

The aforementioned purposes are achieved by the object of the present invention, i.e. a nucleic acid sequence having transcription promoter activity in prokaryotic and/or eukaryotic cell systems.

The transcription is the transfer process of the genetic information from the DNA to the RNA which then will be translated into the protein.

The nucleotide sequence of the invention, having transcription promoter activity in prokaryotic and eukaryotic cell systems, has been arbitrarily called "UnGE" (English acronym of "Universal Gene Expression").

Thus, within the present description we can refer to the nucleotide sequence of the invention having transcription activator activity in prokaryotic and eukaryotic cell systems also with the acronym "UnGE" or "UnGE promoter sequence".

The UnGE promoter sequence of the invention has sequence SEQ. ID. NO. 1:

-UnGE
(SEQ. ID. NO. 1)
CATGATGAAATAACATAAGGTGGTCCCGTCGATAGCCGAAGC

TTACCGAAGTATACACTTAAATTCAGTGCACGTTTGCTTGTTG

AGAGGAAAGGTTGTGTGCGGACGAATTTTTTTTGAAAACATT

AACCCTTACGTGGAATAAAAAAAA

The sequence according to the invention comprises at least one 5'ITR nucleotide sequence of the transposase gene of *Drosophila melanogaster*.

In the present invention, by the term "5'ITR" is meant to denote inverted terminal repeats in 5' of the transposase gene comprised in a P element of *Drosophila melanogaster*.

In molecular biology, a P element is a type of transposable element present in the genome of the Diptera *Drosophila melanogaster*.

The transposable element, also called transposon, is a nucleic acid sequence present in the prokaryotic and eukaryotic genomes able to move from one position to another one of the genome.

The P element comprising the sequence of the invention is a class II transposon. The canonical length of said P elements is 2907 bp and they include the gene coding for the transposase, which is an enzyme catalyzing the excision and integration reactions of the transposable element. Therefore, said P elements are autonomous transposons, able to carry out the transposition thanks to the transposase they code for.

Figure 1:
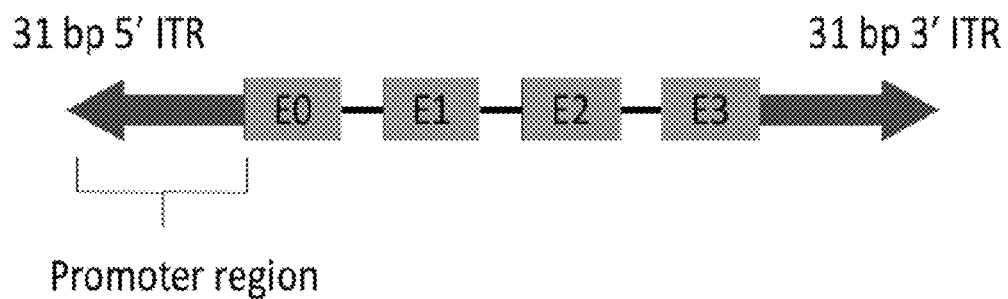
FIG. 1 is a schematic representation of the transposable element P of *Drosophila melanogaster* from which the sequence of the invention has been derived.

The P element comprises inverted terminal repeats (ITR) flanking the transposase gene. Said inverted terminal repeats (ITR) are sequences of 31 bp in 5' and 3' of the transposase gene (FIG. 1). Therefore, 5'ITR sequences are inverted terminal repeats in 5' of the transposase gene in a P element of *Drosophila melanogaster*.

The UnGE promoter sequence according to the invention comprises at least one 5'ITR of a P element of *Drosophila melanogaster*, the length of said 5'ITR being 31 bp.

By the term "5'ITR nucleotide sequence derived from the P element of *Drosophila melanogaster*" is meant herein to refer to all the nucleic acid sequences having a similarity percentage equal to at least 70%, preferably 80%, even more preferably 95% with that of the *Drosophila* species belonging to the *Drosophila* genus.

By way of example, the 5'ITR nucleic acid sequences derived from the P element of other Drosophilidae with a similarity percentage equal to at least 70%, preferably 80%, even more preferably 95% with the 5'ITR nucleotide sequence derived from the P element of *Drosophila melanogaster* are considered sequences similar to the 5'ITR nucleotide sequence derived from the P element of *Drosophila melanogaster*.

Advantageously, it has been found that the UnGE promoter sequence of the invention includes an activating sequence of the transcription of the gene coding for the transposase of the P element.

The length of the UnGE promoter sequence of the invention is between 100 bp and 200 bp, preferably between 120 and 160 bp, even more preferably the length is 152 bp.

Advantageously, the use of an UnGE promoter sequence whose the length is between 100 bp and 200 bp, preferably between 120 and 160 bp, even more preferably is 152 bp, allows obtaining good expression level of nucleic acid sequences of interest in prokaryotic and/or eukaryotic cell systems. Therefore, said UnGE promoter sequence can be used for the ectopic expression of nucleic acid segments of interest in prokaryotic and eukaryotic cell systems.

According to the invention, the UnGE promoter sequence is between the first nucleotide and the nucleotide preceding the first ATG codon of the transposase gene inside the P element of *Drosophila melanogaster*. The ATG codon (triplet AUG on the mRNA) is the specific sequence having 3 nucleotides (triplet) which is used as starting codon of the translation of the mRNA into protein. ATG codon codes for methionine.

Therefore, methionine is the amino acid which occupies the N-terminal of all the proteins of the eukaryotes and archaeobacteria.

According to the invention, the UnGE promoter sequence can be used for the activation of the transcription of at least one nucleic acid sequence of interest in four different host cell systems, for example in prokaryotic host cells and/or eukaryotic host cells. By "host cell system" is meant herein to denote the cell in which nucleic acid sequences of interest, for example gene sequences, are introduced by expression vectors.

Surprisingly, in fact it has been found that the UnGE promoter sequence of the invention is able to operate at the same time as promoter in four different cell systems. In particular, the UnGE promoter sequence is able to activate the transcription of the luciferase gene in bacteria, mammalian cells, yeast and insect cells (Example 2). The luciferase is an enzyme coded by the luc gene of *Photinus pyralis*, used as reporter for the quantitative analysis of elements potentially regulating the gene expression, including the strength of a promoter. The luciferase is also used as reporter protein for the study of the interaction among proteins and nucleic acids and the protein-protein interactions. Therefore, according to the invention, the UnGE promoter sequence is used for the activation of the transcription of at least one nucleic acid sequence of interest in prokaryotic cells, such as for example bacteria, and in eukaryotic cells, such as for example mammalian cells, yeast and insect cells.

According to the invention, the UnGE promoter sequence of the invention is used for the activation of the transcription of at least one nucleic acid sequence of interest when inserted in an expression vector, said expression vector being then introduced in host cell systems. According to an embodiment, the UnGE promoter sequence of the invention is used for the expression of nucleic acid sequences of interest non-coding for proteins. In fact, it is known that some non-coding genome regions, are responsible for the production of regulatory RNAs of the gene expression, such as for example the miRNAs. Said miRNAs are endogenous molecules of non-coding RNAs active in the regulation of the gene expression at the transcriptional and post-transcriptional level.

According to the invention, the UnGE promoter sequence is placed upstream of nucleic acid sequences of interest.

Therefore, in an embodiment, the UnGE promoter sequence of the invention can be placed upstream of nucleic acid non-coding sequences, in order to study the function of new elements of the genome in the basic research.

According to a particularly preferred embodiment, the UnGE promoter sequence of the invention is used for the activation of the transcription of at least one gene sequence of interest. According to said particularly preferred embodiment, the UnGE promoter sequence of the invention is placed upstream of said gene sequences of interest. In particular, said gene sequences of interest are sequences coding for a protein product of interest and comprise the exons of said gene.

The exon is the gene (eukaryotic or of archaeobacteria) part which is transcribed in RNA, together with the introns.

Subsequently, by a process defined splicing, the introns are removed, whereas the exons are linked in the mature RNAs and translated into an amino acid sequence.

It has been observed that the UnGE promoter sequence of the invention has a weak promoter activity. A weak promoter is a promoter able to moderately activate the expression of the sequence of interest placed downstream of it, such as for example a gene. Therefore, said UnGE promoter sequence of the invention is particularly suitable to be used for the expression of proteins of which a medium-low level is desired. Advantageously, the UnGE promoter sequence of the invention is particularly suitable to be used for the expression of proteins which, in high amounts, are toxic for the cell.

Therefore, the UnGE promoter sequence of the invention can be used as weak promoter for the expression of coding sequences or non-coding sequences in prokaryotic and eukaryotic cell systems. For example, the UnGE promoter sequence can be used as weak promoter in prokaryotic cell systems, such as bacteria, and in eukaryotic cell systems, such as mammalian cells and yeast.

Advantageously, it has been observed that the UnGE promoter sequence of the invention doesn't have weak promoter activity when it is used as promoter for the expression of sequences of interest in cells of interest.

Therefore, advantageously, the UnGE promoter sequence can be used in insect cell systems for the expression of proteins of which a high level is desired.

The UnGE promoter sequence of the invention is suitable to be used for the preparation of expression vectors.

It is also an object of the present invention an expression vector comprising the UnGE promoter sequence of the invention. An expression vector according to the invention is a nucleic acid molecule able to carry a nucleic acid sequence in a prokaryotic and/or eukaryotic host cell and able to obtain the expression of said nucleic acid sequence in said host cells. The expression vector comprising the UnGE promoter sequence of the invention has been arbitrarily called "pUnGE". Thus, within the present description we can refer to the expression vector comprising the UnGE promoter sequence also with the acronym "pUnGE".

According to the invention, the expression vector pUnGE comprises the UnGE promoter sequence (SEQ. ID. NO. 1) upstream of a nucleic acid sequence of interest. According to the invention, the expression vector pUnGE further comprises a selection marker, such as for example an antibiotic resistance gene, and an origin of bacterial replication.

Figure 2:
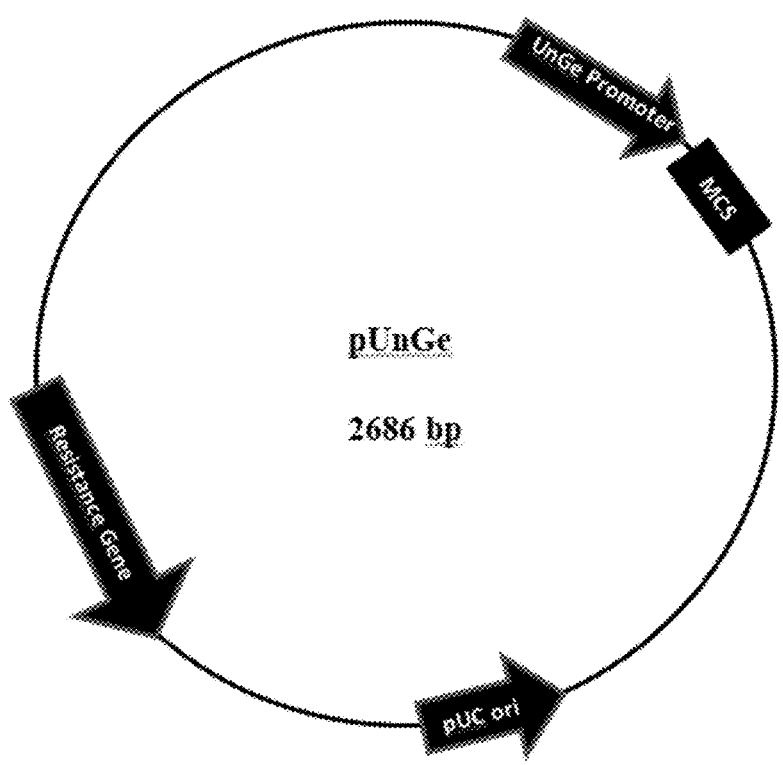
FIG. 2 depicts the expression vector of the invention, comprising the sequence of the invention.

According to a particularly preferred embodiment, the expression vector pUnGE comprises the UnGE promoter sequence upstream of a nucleic acid sequence of interest, said nucleic acid sequence of interest being a gene of interest (transgene). By the term expression vector is meant herein to refer to any nucleic acid molecule for cloning and transferring a nucleic acid in a host cell. By the term "cloning" is meant herein to denote inserting DNA sequences into expression vectors able to transcribe the sequence/gene of interest inside the host cell in which they are inserted. For example, expression vectors according to the invention are considered the plasmid vectors, cosmids, phages, bacterial artificial chromosomes (BAC), yeast artificial chromosomes (YAC), and viral vectors. In FIG. 2 a generic expression vector according to the invention is depicted.

The expression vectors according to the present invention can be prepared according to methods known in the art.

The expression vectors pUnGE according to the present invention overcome the limits of the known art as they allow the transcription of nucleic acid sequences of interest, for example genes, both in prokaryotic cells and eukaryotic cells, without the need to use genetically engineered host systems.

Figure 3:
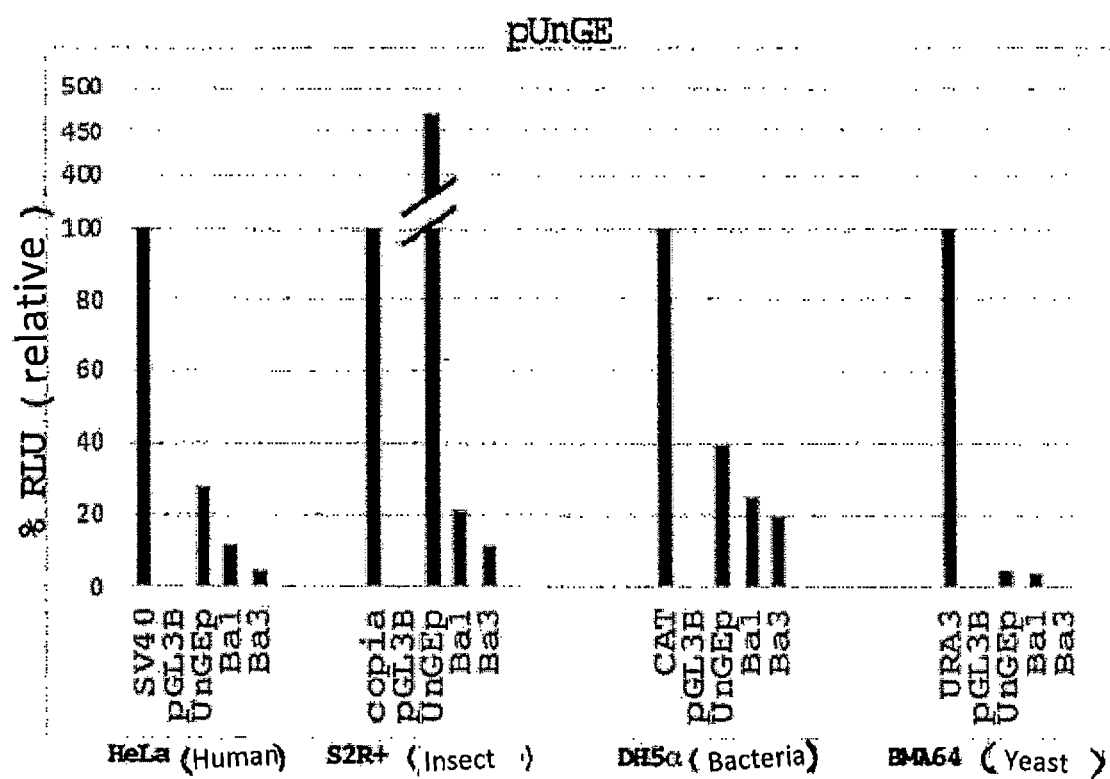
FIG. 3 depicts the results of a bioluminescence assay carried out in four cell systems by comparing different expression vectors with the expression vector comprising the sequence of the invention.

As it is possible to observe in FIG. 3, the expression vector comprising the promoter sequence according to the invention (depicted in FIG. 3 as UnGEp) is able to express the nucleic acid sequence of interest, in the case in question the luciferase gene, also in yeast cells, advantageously at a greater extent with respect to the vector comprising the promoter of the known art UniBa1 upstream of the gene for the luciferase (denoted in FIG. 3 as Ba1). Furthermore, the expression vector of the invention is able to express the luciferase gene more efficiently than the vectors comprising the promoters of the known art UniBa1 and UniBa3 also in mammalian cells, in insect cells and in bacteria.

In light of this, it follows that the expression vectors according to the invention can easily be used for the transfection techniques of any cell line, for example for cultured cell lines for basic research studies on the gene expression, for the production of recombinant proteins or toxicological and pharmacological studies.

By "transfection" is meant herein to denote the introduction process of exogenous biological material in eukaryotic cells, in most cases mammalian cells. The transfection process can be carried out in vitro on target cells in long-term cell cultures, ex vivo on cells isolated from an organism and transferred on culture medium and in vivo directly on cells of an organism.

Furthermore, the expression vectors according to the invention can easily be used for the bacterial transformation and bacterial transduction techniques.

By "transformation" is meant herein to denote a molecular biology technique used to introduce genetic material in bacteria cells.

By "bacterial transduction" is meant to denote the passage of the DNA of a bacterium to another by a phage. A phage, also called bacteriophage, is a virus able to infect the bacterial cells. This allows inserting, in the bacterial genome, a sequence of interest present in the phage, for example a gene sequence.

According to an embodiment, the expression vectors comprising the UnGE promoter sequence of the invention are used for the gene therapy.

By "gene therapy" is meant herein to denote inserting, in specific host cells, expression vectors comprising specific gene sequences of interest in order to cure diseases, preferably genetic diseases.

Therefore, the expression vectors based on the UnGE promoter for the use in gene therapy comprise at least one gene sequence of interest downstream of the UnGE promoter sequence.

The UnGE promoter sequence has non-viral origin and, therefore, involves reduced immunogenicity and cytotoxicity. This allows obtaining safe expression vectors which are suitable for the use in gene therapy.

In another embodiment, the expression vectors of the invention can be used for the trans-kingdom gene therapy. The trans-kingdom gene therapy allows transferring the therapeutic material, in the form of nucleic acids and proteins, to mammalian cells by using cells belonging to different Kingdoms (for example bacteria and fungi) and by the use of expression vectors for the production of the therapeutic material directed to the target cells.

Therefore, by "therapeutic material" is meant herein to denote nucleic acids of interest and proteins of interest introduced in mammalian cells in order to cure diseases.

Surprisingly, the expression vector pUnGE comprising the UnGE promoter sequence is able to transcribe the DNA sequence of interest in bacterial cells in addition to eukaryotic cells, such as for example human, insect and yeast cells (Example 2).

It is a further object of the invention a method for expressing at least one nucleic acid sequence of interest in a prokaryotic and/or eukaryotic host cell, which comprises the steps of:
a) cloning said at least one nucleic acid sequence of interest in an expression vector comprising the UnGE promoter sequence SEQ. ID. NO. 1;
b) introducing said expression vector in the host cell;
c) culturing said prokaryotic and/or eukaryotic host cell under suitable conditions to obtain the expression of said nucleic acid sequence of interest.

According to a preferred embodiment, the expression vector comprises the UnGE promoter sequence of the invention upstream of a gene sequence, transgene.

According to the invention, cloning the DNA sequences of interest inside an expression vector in step a) is carried out by known techniques.

According to the invention, step b) of introducing the expression vector in the host cell can be carried out by transformation or transfection.

Step c) of cultivating the host cell under suitable conditions depends on the type of cell, e.g. prokaryotic cell or eukaryotic cell, and specific cell sub-type, e.g. kidney cell and neuron. The culture conditions of different specific cell sub-types are known in the art and, therefore, step c) of the method according to the invention can be carried out by using known culture conditions.

The use of the UnGE promoter sequence derived from the P element of *Drosophila melanogaster* upstream of a sequence of interest produces a number of unexpected advantages as it allows the activation of the transcription of nucleic acid sequences of interest both in prokaryotic host cells and eukaryotic host cells by simplifying and optimizing the ectopic expression procedures in different cell systems. Advantageously, the expression vector comprising the UnGE promoter sequence of the invention is particularly suitable to be used for the expression of proteins of which a medium-low level is desired. In particular, said expression vector is suitable for the expression of proteins which, in high quantities, are toxic for the cell.

Furthermore, said expression vector can be used for the study of modifiers of the gene expression acting directly on the promoters, such as for example of the repressors or activators of transcription. In fact, by using the expression vector pUnGE comprising an UnGE promoter sequence having weak promoter activity, the effect of the expression modifiers, for example having repression effects of the transcription, would immediately be evident by the drastic drop of the protein level. By using the expression vector pUnGE comprising an UnGE promoter sequence having weak promoter activity, the effect of the expression modifiers, for example having activation effects of the transcription, would immediately be evident by the very large amount of protein.

Still more advantageously, the expression vector comprising the UnGE promoter sequence of the invention is a valid alternative to the expression vectors currently available. In fact, the sequence of the invention and the expression vectors comprising it allow to quickly switch from experiments and assays in one cell system to another of different origin. It follows that the chosen procedures of the final platform for the expression of a sequence of interest, such as for example a transgene (and related recombinant protein) will be greatly accelerated.

A further advantage arise from the fact that, by introducing the expression vector based on the use of the UnGE promoter, the analysis of the gene expression or sequences of interest will be able to be carried out in parallel after a single cloning operation in the pUnGE vector at the level of prokaryotic cell systems and eukaryotic cell systems, for example in mammalian cells, insect, yeast and bacterium cells. In other words, a unique vector comprising the nucleotide sequence of interest will be able to be inserted in the four cell systems mentioned above to carry out parallel experiments. Therefore, the UnGE promoter sequence of the invention and the expression vector comprising said sequence will allow reducing the research costs since it will no longer be necessary to build or buy other expression vectors known for being used for specific types of cells.

Advantageously, analysis and production times of recombinant products at any level (basic research, industrial production of therapeutic proteins etc.) may also be reduced because only one expression vector comprising an UnGE promoter sequence will be sufficient to carry out the analysis and production of proteins in multiple host cell systems.

DESCRIPTION OF THE FIGURES

FIG. 1 is a schematic representation of a canonical P element of *Drosophila melanogaster*. Said P element comprises the UnGE promoter sequence of the invention in the element portion depicted by the brace that includes the 5' ITR portion. The transposase gene in a canonical P element comprises four exons (E0, E1, E2 and E3) and three introns between E0 and E1, E1 and E2, and E2 and E3.

FIG. 2 depicts a generic plasmid expression vector comprising the UnGE promoter sequence of the invention. In FIG. 2 are also schematized an origin of bacterial replication (depicted in Figure as pUC ori) and an antibiotic resistance gene (depicted in Figure as Resistance Gene).

FIG. 3 depicts the results of a bioluminescence assay carried out with five different expression vectors in four host cell systems. The host cell systems are depicted on the abscissa of the graph and are human HeLa cells, cells of *Drosophila melanogaster* S2R+, bacterium DH5α and yeast (BMA64).

The expression vectors used for the bioluminescence assay are also depicted on the abscissa of the graph. The expression vectors containing different promoters upstream of the luciferase gene are depicted in FIG. 3 as UnGEp (vector comprising the UnGE promoter sequence of the invention), Ba1 (comprising the UniBa1 promoter sequence), Ba3 (comprising the UniBa3 promoter sequence). Ba1 and Ba3 are expression vectors known in the art to have promoter activity both in prokaryotic cell systems and eukaryotic cell systems. The activity of the UnGE promoter sequence is compared with that of said promoters known in the art.

The negative control is depicted in FIG. 3 as "pGL3B".

The positive controls are different for each host cell. In FIG. 3, the positive controls are depicted as SV40, copy, CAT and URA 3.

The bioluminescence results are expressed as relative light units % (Relative Light Units, RLU). The RLU % is depicted in the ordinate of the graph in FIG. 3.

EXPERIMENTAL SECTION

Example 1: Construction of the Expression Vector Comprising the UnGE Promoter Sequence of the Invention The UnGE promoter sequence of the invention (SEQ ID. NO. 1) has been cloned in the pGL3B-Basic plasmid expression vector (Promega Corporation) upstream of the gene sequence of luciferase. Such pGL3-Basic vector contains a reporter gene coding the luciferase enzyme of the *Photinus pyralis* firefly.

The plasmid has been cut with restriction enzymes XhoI and NcoI so as to be linearized.

For the following experiment, the UnGE promoter sequence of the invention has been amplified by primers having at their ends the sequences recognized by the restriction enzymes XhoI and NcoI.

Amplified UnGE promoter sequence obtained by using as template the "pCasper3" clone (Acc. No. GenBank U59055) and using the primers:

```
PrimerUnGE_fw (forward):
                                       (SEQ. ID. NO. 2)
gatcctcgagCATGATGAAATAACATAAGGTG PrimerUnGE_rev (reverse):
                                       (SEQ. ID. NO. 3)
gatcccatggTTTTTTTTATTCCACGTAAGGGT
```

The PCR reactions to obtain the amplified UnGE promoter sequence have been carried out in standard conditions as mentioned.
Thermal Cycling Parameters
1 Cycle:
  Denaturation for 3' at 94° C.
35 Cycles:
  Denaturation for 30" at 94° C.
  Annealing for 30" at 48° C.
  Elongation for 20" at 72° C.
1 Cycle:
  7' at 72° C.
  4° C.∞
The reaction mixture for the amplification of the UnGE promoter sequence is constituted as follows:

| Reaction buffer | 1× |
|---|---|
| Mg2+ | 1.5 mM |
| dNTP mix | 0.2 mM |
| primer UnGE_fw | 0.4 μM |
| primer UnGE_rev | 0.4 μM |
| Platinum Taq | 1 U |
| Template DNA | 1-5 ng |
| Water | up to 50 μl |

The enzyme used is Platinum Taq polymerase (Invitrogen, Life Technologies).

The oligonucleotides PrimerUnGE fw (forward) (SEQ. ID. NO. 2) and PrimerUnGE rev (reverse) (SEQ. ID. NO. 3) contain target sequences for the restriction enzyme XhoI and NcoI (depicted in lowercase in the primer sequences). The obtained amplification fragments have been cloned in the XhoI and NcoI sites of the plasmid vector pGL3-Basic (PROMEGA).

The enzymatic digestion of the amplified UnGE promoter sequence and pGL3-B vector has been carried out with the following method.

Digestion Reaction for the PCR Samples

| Amplified UnGE | 1 μg |
|---|---|
| Buffer H (NEB) | 1× |
| Enzyme NcoI (NEB) | 2 U |
| Enzyme XhoI (NEB) | 2 U |
| Water | up to 25 μl |

The reactions have been carried out for 2 h at 37° C.
Digestion Reaction for the pGL3-B Plasmid

| DNA pGL3-B | 1 μg |
|---|---|
| Buffer H NEB 10× | 1× |
| Enzyme NcoI NEB | 2 U |
| Enzyme XhoI NEB | 2 U |
| Water | up to 25 μl |

The reactions have been carried out for 2 h at 37° C.
Ligation of the Digested Fragments

| T4 DNA Ligase Reaction Buffer | 1× |
|---|---|
| Digested pGL3B | 50 ng |
| UnGE promoter sequence | 100 ng |
| T4 DNA ligase (NEB) | 1 U |
| Water | up to 20 μl |

Reactions carried out at 15° C. for about 16 hours.

The recombinant plasmid clones have been purified with commercial kits (QIAGEN plasmid mini kit), quantified by measurement at Nanodrop and subsequently 1 μg of each single plasmid has been carried to the cells of interest.

The cloned fragment, i.e. the UnGE promoter sequence of the invention and the luciferase gene downstream of said sequence, has been sequenced to verify the correctness of the sequence itself.

Example 2: Luciferase Assay for the Definition of the Activity of the Promoter of the Invention An expression vector comprising the UnGE promoter sequence of the invention, as it was generated in the example 1, has been used in the luciferase assay in four different cell systems. Said expression vector comprises the UnGE promoter sequence of the invention upstream of the luciferase gene and is called pUnGE.

To test the efficiency of the UnGE promoter sequence in the transcription of the luciferase gene, a bioluminescence assay has been fine-tuned.

In the bioluminescence assay, in each host cell system have been tested five different expression vectors: three expression vectors each comprising a different promoter upstream of the luciferase gene, a negative control and a positive control. For all of the expression vectors the commercially available plasmid named pGL3-Basic (Promega Corporation) has been used. In fact, the pGL3-Basic plasmid is particularly useful with the purpose of measuring the promoter activity thanks to the presence of a synthetic polyadenylation sequence upstream of the multiple cloning site (MCS), reducing the transcriptional background due to non-specific sequence.

The three expression vectors comprising three different promoters upstream of the gene for the luciferase are:
  pGL3B-UnGE comprising the UnGE promoter sequence
  pGL3B-Uniba1 comprising the UniBa1 promoter sequence, depicted herein below.

UniBa1
(SEQ. ID NO. 4)
CAGTCATGGTCAAAATTATTTTCACAAAGTGCATTTTTGTGCA

TGGGTCACAAACAGTTGCTTGTGCAGCAAGTGGGGGAGGTG

AAATGCAAAAAAACTTTTGCTTTTGCAAATTCAAACCTATGCA

GAGTCAGATGAAAGAAGAATTGAAAAAATAACTGTTCCTATG

CGCAAGGAAGAGGCAAATGAAGAGATCTTTATCAGTTGTCAG

AAGTATTTGCACACGGTTTCGTCGCATCACAATTATTTTCACA

ACGCAATTTCTTCTTCAGTGATTGGTTTAGAGTGACAAGTGCC

GGTTTGTTTGCTTAAATACATTTAAATTATTGAATAAAAATTA

GATTTAATCATTTTCCTATTACAGTTATTAAATAAA pGL3B-Uniba3 comprising the UniBa3 promoter sequence, depicted herein below.

UniBa 3:
(SEQ. ID. NO. 5)
CAGAGGTGGTCAAAAGTAATTACACACCGAGCTTTTTTCTGCA

TGCTCAGCTTTAAAAGCTTGTTGTTGTTGTTGTTCGCTGTT

TTTGAAAAAAAGCTTTTGTGTCATAAAGCTTATTCTGTGTAGA

AGCGATCGGCAAAAAGAAATTGCTAAAATAACGGTACAGGTT

CGTAGATATAGCAAAAAGAACAGTTACCTAGAGGTTGTCAAA

AGTATTTACACACATTTTTTTTGCGTCATAAGTATTTACACAAT

GTAAATTTGCCTTTAGTCTTTGATTTGCGTTGATCATGTGCGGT

CTTTGACTAAGATCGGAATTCAATTTGTAGTTGAAATTGTAGA

TGTGCTGTAAA.

UniBa1 and UniBa3 are two promoter sequences having activator activity of the gene transcription in prokaryotic and eukaryotic cell systems. Said sequences have been used as comparative sequences with which to compare the activity of the UnGE promoter sequence.

The negative control is the plasmid not comprising a promoter upstream of the luciferase gene (pGL3B).

The positive controls provide a bioluminescence reference value in the four cell systems and are different for each host cell.

pGL3B-copy provides a bioluminescence reference value in insect cell systems. It is a plasmid comprising the promoter of the copy retro-transposon, widely used for the expression in *Drosophila*. It has been amplified starting from the pCoBlast plasmid, sold by Life Technologies as part of the DES®-Inducible Kit expression system.

pGL3B-cat comprises the promoter of the CAT (chloramphenicol acetyl transferase) gene and is used because it provides a bioluminescence reference value in the bacteria. Said CAT promoter has been amplified starting from the pHSG396 plasmid containing the entire expression cassette for the chloramphenicol acetyl transferase.

pGL3-promoter vector contains the SV40 promoter of viral origin and represents the bioluminescence reference value in the human HeLa cells. The pGL3-promoter vector plasmid is sold by Promega (catalog number E1761).

pFL39-URA contains the promoter gel gene URA3 of yeast and provides a bioluminescence reference value in the yeast. Said URA promoter has been amplified starting from the pFL44 plasmid containing the entire expression cassette of the URA3 gene of *Saccharomyces cerevisiae*.

The plasmid DNAs have been extracted with commercial purification kits, quantified by reading on Nanodrop and, subsequently, 1 µg of each single plasmid has been introduced in the host cell system of interest. The transfection method is different for eukaryotic and prokaryotic cells. For the transfection in eukaryotic cells, the MIRUS TransIt_LT1 (Mirus Bio LLC) transfection agent has been used as specified in the supplier manual, whereas in the case of prokaryotic cells, the procedure of calcium chloride has been used. Said expression vectors have been introduced in four cell systems: human HeLa cells, cells of *Drosophila melanogaster* S2R+, *E. coli* DH5α bacterium and in *S. cerevisiae* BMA64 yeast.

The cell systems used for the purpose of determining the activity of the promoters in the tested expression vectors are:
DH5α™ (InvITRogen) (F-Φ80lacZΔM15 Δ(lacZYA-argF) U169 recA1 endA1 hsdR17 (Rk–, Mk+) phoA supE44 λ-thi-1 gyrA96 relA1)
*Drosophila* S2R+(DGRC) derived from the Schneider's line 2 (Schneider, I. (1972). Cell lines derived from late embryonic stages of *Drosophila melanogaster*. J. Embryol. exp. Morphol. 27:353-365)
HeLa cervical cancer cells (ATCC)
*S. cerevisiae* BMA64-1A (MAT a ura 3-1 ade 2-1 leu 2-3, 112 his3-11,15 trp1D can 1-100).

Each expression assay has been carried out in triplicate on a suitable number of cells, variable depending to the cell type used as experimental model, but which always refers to procedures normally used in analogous assays.

The expression level of the luciferase gene, and thus the amount of the protein, has been evaluated based on the amount of light emitted. In fact, the luciferase is able to catalyze a particular chemical reaction, during which chemical energy is converted into light energy.

The bioluminescence results are expresses as relative light units % (Relative Light Units, RLU in the ordinate).

RLU % detected is directly proportional to the level of synthesized protein and, therefore, to the expression level of the luciferase gene downstream of the various tested promoters. RLU % of the positive control was arbitrarily set equal to 100%.

As it is possible to observe in FIG. 3, the expression vector pUnGE comprising the UnGE promoter sequence (depicted in FIG. 3 as UnGEp) in *Drosophila* cells gives a high expression level of the luciferase gene, higher than that of the positive control. In fact, the % of relative light units detected is equal to at least 450%.

Furthermore, from FIG. 3 it is possible to observe that the UnGEp promoter is able to express the sequence of interest, luciferase gene, also in yeast cells, advantageously at a greater extent than the vector comprising the UniBa1 promoter upstream of the gene for the luciferase (depicted in FIG. 3 as Ba1). Furthermore, the pUnGE expression vector comprising the UnGE promoter sequence of the invention is able to express the luciferase gene more efficiently than the UniBa1 and UniBa3 promoters known in the art (contained in the pUniBa1 and pUniBa3 expression vectors) also in mammalian cells, insect cells and bacteria.

The invention claimed is:

1. A method of expressing at least one nucleic acid sequence of interest in a prokaryotic and/or eukaryotic host cell, comprising the steps of:
a) cloning said at least one nucleic acid sequence of interest in an expression vector comprising an isolated nucleic acid sequence having SEQ ID NO: 1;
b) introducing said expression vector in the prokaryotic and/or eukaryotic host cell;
c) culturing said prokaryotic and/or eukaryotic host cell under suitable conditions to obtain the expression of said nucleic acid sequence of interest;
wherein said isolated nucleic acid sequence having SEQ ID NO: 1 acts as a promoter to express said at least one nucleic acid sequence of interest.

2. The method according to claim 1, wherein said prokaryotic host cell is a bacterium and said eukaryotic host cell is selected from mammalian cells, yeast and insect cells.

* * * * *

SEQUENCE LISTING

```
Sequence total quantity: 5
SEQ ID NO: 1                moltype = DNA   length = 152
FEATURE                     Location/Qualifiers
misc_feature                1..152
                            note = promoter sequence UnGE derived from Drosophila
source                      1..152
                            mol_type = other DNA
                            organism = synthetic construct
SEQUENCE: 1
catgatgaaa taacataagg tggtcccgtc gatagccgaa gcttaccgaa gtatacactt   60
aaattcagtg cacgtttgct tgttgagagg aaaggttgtg tgcggacgaa ttttttttttg  120
aaaacattaa cccttacgtg gaataaaaaa aa                                 152

SEQ ID NO: 2                moltype = DNA   length = 32
FEATURE                     Location/Qualifiers
misc_feature                1..32
                            note = PrimerUnGE_fw (forward)
source                      1..32
                            mol_type = other DNA
                            organism = synthetic construct
SEQUENCE: 2
gatcctcgag catgatgaaa taacataagg tg                                 32

SEQ ID NO: 3                moltype = DNA   length = 33
FEATURE                     Location/Qualifiers
misc_feature                1..33
                            note = PrimerUnGE_rev (reverse)
source                      1..33
                            mol_type = other DNA
                            organism = synthetic construct
SEQUENCE: 3
gatcccatgg ttttttttat tccacgtaag ggt                                33

SEQ ID NO: 4                moltype = DNA   length = 377
FEATURE                     Location/Qualifiers
misc_feature                1..377
                            note = Promoter sequence UniBa1
source                      1..377
                            mol_type = other DNA
                            organism = synthetic construct
SEQUENCE: 4
cagtcatggt caaaattatt ttcacaaagt gcattttgt gcatgggtca caaacagttg    60
cttgtgcagc aagtgggggg aggtgaaatg caaaaaaact tttgcttttg caaattcaaa   120
cctatgcaga gtcagatgaa agaagaattg aaaaaataac tgttcctatg cgcaaggaag   180
aggcaaatga agagatcttt atcagttgtc agaagtattt gcacacggtt tcgtcgcatc   240
acaattattt tcacaacgca atttcttctt cagtgattgg tttagagtga caagtgccgg   300
tttgtttgct taaatacatt taaattattg aataaaaatt agatttaatc attttcctat   360
tacagttatt aaataaa                                                  377

SEQ ID NO: 5                moltype = DNA   length = 356
FEATURE                     Location/Qualifiers
misc_feature                1..356
                            note = Promoter sequence UniBa3
source                      1..356
                            mol_type = other DNA
                            organism = synthetic construct
SEQUENCE: 5
cagaggtggt caaagtaat tacacaccga gctttttct gcatgctcag ctttaaaagc     60
ttgttgttgt tgttgttgtt cgctgttttt gaaaaaaagc ttttgtgtca taagcttat    120
tctgtgtaga agcgatcggc aaaaagaaat tgctaaaata acggtacagg ttcgtagata   180
tagcaaaaag aacagttacc tagaggttgt caaaagtatt tacacacatt ttttttgcgt   240
cataagtatt tacacaatgt aaatttgcct ttagtctttg atttgcgttg atcatgtgcg   300
gtctttgact aagatcggaa ttcaatttgt agttgaaatt gtagatgtgc tgtaaa       356
```